United States Patent
Lin et al.

(10) Patent No.: US 9,983,190 B2
(45) Date of Patent: May 29, 2018

(54) NANOFLUIDIC CHANNELS WITH GRADUAL DEPTH CHANGE FOR REDUCING ENTROPIC BARRIER OF BIOPOLYMERS

(71) Applicant: INTERNATIONAL BUSINESS MACHINES CORPORATION, Armonk, NY (US)

(72) Inventors: Qinghuang Lin, Yorktown Heights, NY (US); Gustavo A. Stolovitzky, Riverdale, NY (US); Chao Wang, Ossining, NY (US); Deqiang Wang, Ossining, NY (US)

(73) Assignee: International Business Machines Corporation, Armonk, NY (US)

( * ) Notice: Subject to any disclaimer, the term of this patent is extended or adjusted under 35 U.S.C. 154(b) by 240 days.

(21) Appl. No.: 15/085,394

(22) Filed: Mar. 30, 2016

(65) Prior Publication Data

US 2016/0209394 A1    Jul. 21, 2016

Related U.S. Application Data

(63) Continuation of application No. 13/944,552, filed on Jul. 17, 2013, now Pat. No. 9,364,832.

(51) Int. Cl.
*G01N 33/487* (2006.01)
*B01L 3/00* (2006.01)

(52) U.S. Cl.
CPC .. *G01N 33/48721* (2013.01); *B01L 3/502715* (2013.01); *B01L 3/502761* (2013.01); *B01L 2300/042* (2013.01); *B01L 2300/0645* (2013.01); *B01L 2300/0887* (2013.01); *B01L 2300/0896* (2013.01); *B01L 2300/161* (2013.01)

(58) Field of Classification Search
None
See application file for complete search history.

(56) References Cited

U.S. PATENT DOCUMENTS

| | | | |
|---|---|---|---|
| 5,932,799 A * | 8/1999 | Moles | B01L 3/502707 73/53.01 |
| 5,989,445 A | 11/1999 | Wise et al. | |
| 6,685,841 B2 | 2/2004 | Lopez et al. | |
| 6,696,022 B1 | 2/2004 | Chan et al. | |
| 7,217,562 B2 | 5/2007 | Cao et al. | |

(Continued)

OTHER PUBLICATIONS

Non-Final Office Action for U.S. Appl. No. 13/971,166 dated Jun. 17, 2015.

(Continued)

*Primary Examiner* — Luan V Van
*Assistant Examiner* — Steven E Rosenwald
(74) *Attorney, Agent, or Firm* — Tutunjian & Bitetto, P.C.; Vazken Alexanian

(57) ABSTRACT

A device for passing a biopolymer molecule includes a nanochannel formed between a surface relief structure, a patterned layer forming sidewalls of the nanochannel and a sealing layer formed over the patterned layer to encapsulate the nanochannel. The surface relief structure includes a three-dimensionally rounded surface that reduces a channel dimension of the nanochannel at a portion of nanochannel and gradually increases the dimension along the nanochannel toward an opening position, which is configured to receive a biopolymer.

10 Claims, 10 Drawing Sheets

(56) References Cited

U.S. PATENT DOCUMENTS

| | | |
|---|---|---|
| 7,985,689 B2 | 7/2011 | Perozziello et al. |
| 8,137,569 B2 | 3/2012 | Harnack et al. |
| 2005/0136419 A1 | 6/2005 | Lee |
| 2009/0023146 A1* | 1/2009 | Harnack ........... B01L 3/502761 435/6.12 |
| 2014/0151227 A1 | 6/2014 | Royyuru et al. |

OTHER PUBLICATIONS

Ando, G., et al. "Directly Observing the Motion of DNA Molecules Near Solid-State Nanopores" ACS Nano, vol. 6, No. 11. Oct. 2012. pp. 10090-10097.

Audran, S., et al. "Study of Dynamical Formation and Shape of Microlenses Formed by the Reflow Method" Advances in Resist Technology and Processing XXIII. Proceedings of SPIE, vol. 6153. Mar. 2006. pp. 1-10.

Branton, D., et al. "The Potential and Challenges of Nanopore Sequencing" Nature Biotechnology, vol. 26, No. 10. Oct. 2008. pp. 1146-1153.

Cao, H., et al., "Gradient Nanostructures for Interfacing Microfluidics and Nanofluidics" Applied Physics Letters, vol. 81, No. 16. Oct. 2002. pp. 3058-3060.

Dekker, C. "Solid-State Nanopores" Nature Nanotechnology. Mar. 2007. pp. 209-215.

Firnkes, M., et al. "Electrically Facilitated Translocations of Proteins Through Silicon Nitride Nanopores: Conjoint and Competitive Action of Diffusion, Electrophoresis, and Electroosmosis" Nano Letters, vol. 10. May 2010. pp. 2162-2167.

Fu, J., et al. "A Patterned Anisotropic Nanofluidic Sieving Structure for Continuous-Flow Separation of DNA and Proteins" Nature Nanotechnology, vol. 2. Feb. 2007. pp. 121-128.

Han, J., et al. "Entropic Trapping and Escape of Long DNA Molecules At Submicron Size Contriction" Physical Review Letters, vol. 83, No. 8. Aug. 1999. pp. 1688-1691.

He, M., et al., "A High-Corrugation-Rate Self-Processing $SiO_2$—$ZrO_2$ Hybrid Sol-Gel Material for Fabrication of Microlens Array" IEEE Photonics Technology Letters, vol. 17, No. 6. Jun. 2005. pp. 1223-1225.

He, M., et al., "Simple Reflow Technique for Fabrication of a Microlens Array in SolGel Glass" Optics Letters, vol. 28, No. 9. May 2003. pp. 731-733.

Leslie, S., et al., "Convex Lens-Induced Confinement for Imaging Single Molecules" Analytical Chemistry, vol. 82, No. 14. Jul. 2010. pp. 6224-6229.

Levy, S., et al. "Entropic Unfolding of DNA Molecules in Nanofluidic Channels" Nano Letters, vol. 8, No. 11. Oct. 2008. p. 3839-3844.

Meller, A., et al. "Voltage-Driven DNA Translocations Through a Nanopore" Physical Review Letters, vol. 86, No. 15. Apr. 2001. pp. 3435-3438.

Reisner, W., et al. "Statics and Dynamics of Single DNA Molecules Confined in Nanochannels" Physical Review Letters, vol. 94. May 2005. pp. 1-4.

Tegenfeldt, J., et al. "The Dynamics of Genomic-Length DNA Molecules in 100-nm Channels" PNAS 2004, vol. 101, No. 30. Jul. 2004. pp. 10979-10983.

Wang, C., et al., "Fabrication of a 63-nm-Diameter Perfectly Round Metal-Dot Array Over a Large Area on a Plastic Substrate Using Nanoimprint Lithography and Self-Perfection by Liquefaction" Small 2010, vol. 6, No. 11. Jun. 2010. pp. 1242-1247.

* cited by examiner ized
NANOFLUIDIC CHANNELS WITH GRADUAL DEPTH CHANGE FOR REDUCING ENTROPIC BARRIER OF BIOPOLYMERS

BACKGROUND

Technical Field

The present invention relates to nanodevices, and more particularly to devices and methods for stretching biopolymers using nanofluidic channels.

Description of the Related Art

Accurate and inexpensive sensing of biopolymers, especially nucleic acids (DNA, RNA), is important for many scientific and biomedical applications. A high-throughput and robust device to electrically sequence the biopolymers is of great importance. Solid-state bio-sensing techniques, such as artificial nanopores and channels, have been integrated into fluidics for sensing (sequencing) many types of biopolymer molecules, including DNA, RNA, proteins, etc. For precise single molecule sensing of biopolymers, a linearized or fully stretched biopolymer chain conformation is desirable. However, thermodynamically favored conformation of flexible biopolymers, such as a single strain DNA, includes a coiled conformation. One key issue for sensing biopolymers is a large entropic energy barrier for biopolymers (e.g., low entropy for stretched biopolymers and high entropy for coiled ones) to be transported from a large dimension into a smaller dimension. Such a large energy barrier originates from the entropic difference of the flexible polymer.

A large energy barrier greatly lowers the translocation rate of the biopolymers, and can cause very long clogging events in nano-scale channels. Such a large entropy change can cause configurational instabilities of the biopolymers and even drive them to randomly coil and decoil inside the nanofluidic channels or pores. All of these and other problems can lead to reduced and clogged events and thus severely affect proper detection of molecules. Moreover, the entropic energy barrier height increases with the biopolymer chain length, making it very undesirable for precise and high-speed sensing of long biopolymers.

SUMMARY

A device for passing a biopolymer molecule includes a nanochannel formed between a surface relief structure, a patterned layer forming sidewalls of the nanochannel and a sealing layer formed over the patterned layer to encapsulate the nanochannel. The surface relief structure includes a three-dimensionally rounded surface that reduces a channel dimension of the nanochannel at a portion of nanochannel and gradually increases the dimension along the nanochannel toward an opening position, which is configured to receive a biopolymer.

Another device for passing a biopolymer molecule includes a substrate, and a surface relief structure formed on the substrate and having at least one three-dimensionally rounded surface providing a gradually changing depth from a position on the surface relief structure along a channel. The surface relief structure forms a first surface of the channel. A patterned layer is formed on the surface relief structure and forms sidewalls of the channel. A sealing layer is formed over the patterned layer to form a second surface of the channel opposite the first surface.

A method for fabricating a device for evaluating biopolymer molecules includes patterning a surface relief material on a substrate; annealing the surface relief material to reflow the surface relief material to form a surface relief structure that includes a rounded surface; planarizing a channel dielectric layer formed over the surface relief material; patterning the channel dielectric layer to shape a nanochannel over the surface relief material; and forming a sealing layer over the channel dielectric layer to encapsulate a channel, wherein the channel includes a channel dimension at a portion of nanochannel and gradually increases the dimension along the nanochannel toward an opening position, which is configured to receive a biopolymer.

These and other features and advantages will become apparent from the following detailed description of illustrative embodiments thereof, which is to be read in connection with the accompanying drawings.

BRIEF DESCRIPTION OF DRAWINGS

The disclosure will provide details in the following description of preferred embodiments with reference to the following figures wherein.

DETAILED DESCRIPTION OF PREFERRED EMBODIMENTS

Figure 1A:
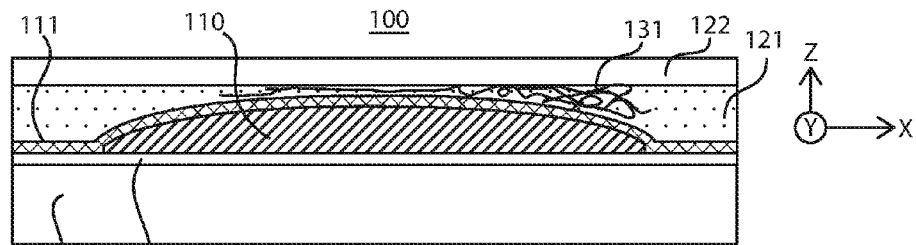
FIG. 1A is a cross-sectional view of a fluidic channel device with gradually changing depth for reduction of entropic barrier in accordance with the present principles.

In accordance with the present principles, a nanodevice includes a nanochannel having a patterned and reflowed surface relief material to form micro- or nano-scale caps. Such caps can be controlled to have gradual changes in thickness, and serve as a scaffold to define a channel bottom surface, hence yielding a gradually changing channel depth. A flexibly tuned and gradually changing channel depth permits minimized entropic barrier for molecules to translocate. Electrodes can be integrated into the channels for controlling the molecular motion or molecular sensing.

A method for fabricating nanofluidic channels with gradually changing depth are provided by building such channels on a surface relief material with a tunable curvature. The curvature of the surface relief material can be designed by engineering its volume, shape, and contact angle on an underlying substrate. Using this, the channel depth and hence confinement of biopolymers can be accurately and flexibly optimized. This can minimize the entopic barrier of the biopolymer to enter into a narrowest channel region and yield a higher translocation rate.

It is to be understood that the present invention will be described in terms of a given illustrative architecture having a wafer, substrate or other solid-state material; however, other architectures, structures, substrate materials and process features and steps may be varied within the scope of the present invention.

It will also be understood that when an element such as a layer, region or substrate is referred to as being "on" or "over" another element, it can be directly on the other element or intervening elements may also be present. In contrast, when an element is referred to as being "directly on" or "directly over" another element, there are no intervening elements present. It will also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

A design for an integrated circuit chip or nanodevice may be created in a graphical computer programming language, and stored in a computer storage medium (such as a disk, tape, physical hard drive, or virtual hard drive such as in a storage access network). If the designer does not fabricate chips or the photolithographic masks used to fabricate chips, the designer may transmit the resulting design by physical means (e.g., by providing a copy of the storage medium storing the design) or electronically (e.g., through the Internet) to such entities, directly or indirectly. The stored design is then converted into the appropriate format (e.g., GDSII) for the fabrication of photolithographic masks, which typically include multiple copies of the chip design in question that are to be formed on a wafer. The photolithographic masks are utilized to define areas of the wafer (and/or the layers thereon) to be etched or otherwise processed.

Methods as described herein may be used in the fabrication of integrated circuit chips or nanodevices. The resulting integrated circuit chips can be distributed by the fabricator in raw wafer form (that is, as a single wafer that has multiple unpackaged chips), as a bare die, or in a packaged form. In the latter case the chip is mounted in a single chip package (such as a plastic carrier, with leads that are affixed to a motherboard or other higher level carrier) or in a multichip package (such as a ceramic carrier that has either or both surface interconnections or buried interconnections). In any case the chip is then integrated with other chips, discrete circuit elements, and/or other signal processing devices as part of either (a) an intermediate product, such as a motherboard, or (b) an end product. The end product can be any product that includes integrated circuit chips, ranging from toys and other low-end applications to advanced computer products having a display, a keyboard or other input device, and a central processor.

Reference in the specification to "one embodiment" or "an embodiment" of the present principles, as well as other variations thereof, means that a particular feature, structure, characteristic, and so forth described in connection with the embodiment is included in at least one embodiment of the present principles. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C).

This may be extended, as readily apparent by one of ordinary skill in this and related arts, for as many items listed.

Figure 1B:
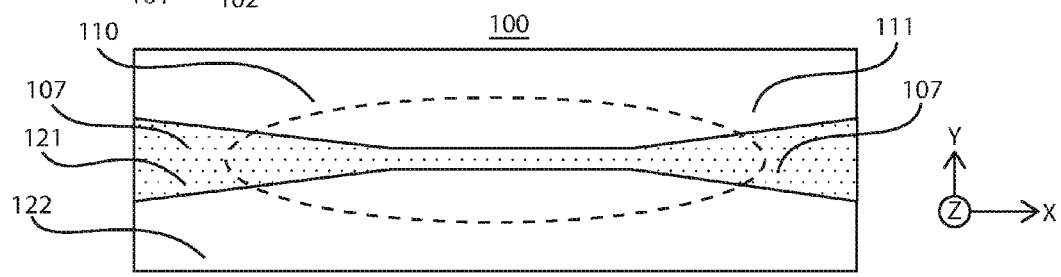
FIG. 1B is a top-view of the channel of FIG. 1A.

Referring now to the drawings in which like numerals represent the same or similar elements and initially to FIGS. 1A and 1B, a nanodevice or nanofluidic structure 100 includes a fluidic channel 121 with gradually changing depth for the reduction of entropic barrier in accordance with one illustrative embodiment. FIG. 1A shows a cross-sectional view and FIG. 1B shows a top view of the nanofluidic structure 100. The nanofluidic structure 100 includes a substrate material 101 coated with a surface coating layer 102. The substrate material 101 may include, e.g., an insulator, a semiconductor, conductor or another suitable rigid material. The surface coating layer 102 may include self-assembled monolayer (SAM, e.g., a single layer of organic molecules), dielectric, metal, glass, semiconductor, etc. A surface relief material or cap 110 may be formed in place or shaped by reflow. Surface relief material or structure 110 may be formed in a spherical cap shape or any other shape having a gradual changing profile. Surface relief material 110 may include a glass, a resist, a polymer, such as polycarbonate, polyethylene, poly (methyl methacrylate) (PMMA), a metal (e.g., a solder), etc.

An optional dielectric layer 111 may be employed to coat the surface relief cap 110. The dielectric layer 111 may be employed to control a dimension of the nanofluidic channel 121 and is formed in an insulating material on top of the coated spherical cap 110. A dielectric material 122 seals the nanofluidic channel 121. A biopolymer 131, e.g., a DNA molecule, is illustratively shown to demonstrate operation of the nanofluidic structure 100. The nanofluidic channel 121 may include a larger feed port 107 and/or exit port 107 in communication with the nanofluidic channel 121.

Figure 2:
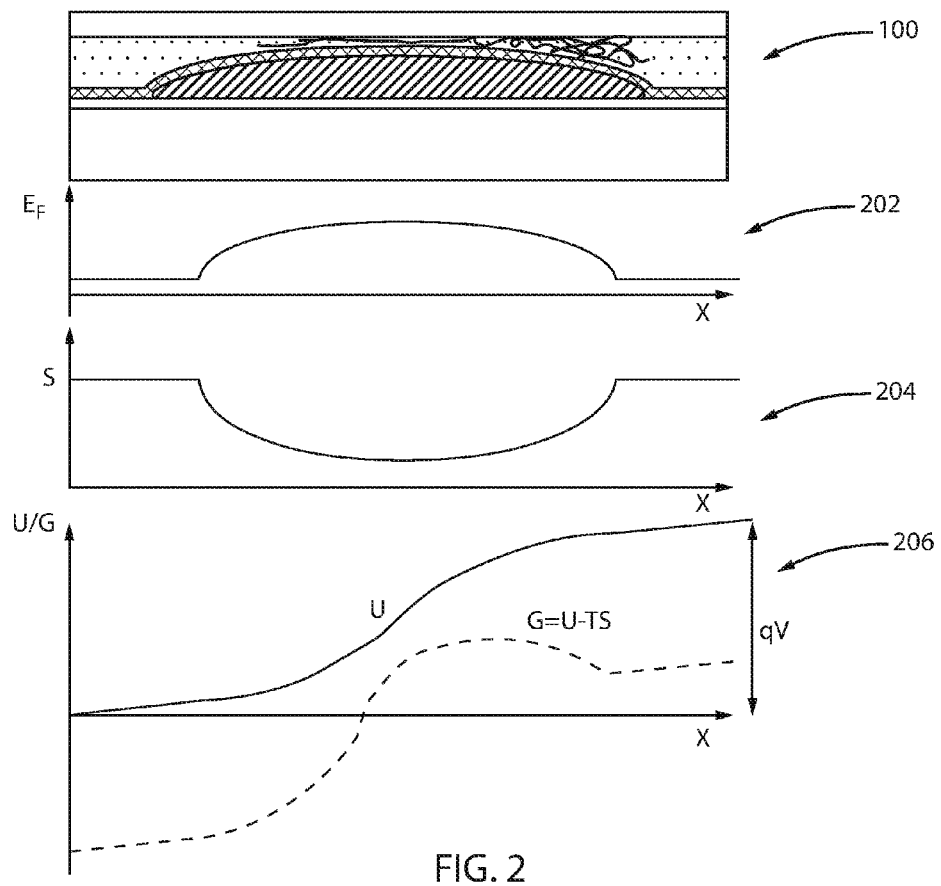
FIG. 2 shows the fluidic channel device of FIG. 1 along with an electric field distribution graph along the channel, an entropy (S) graph of DNA along the channel and graphs of electrostatic energy (U) and Gibbs free energy (G=U−T*S) of DNA in accordance with the present principles.

Referring to FIG. 2, the nanofluidic structure 100 with a gradually changing nano-fluidic channel depth for reduction of an entropic barrier is depicted in cross-section. A graph 202 shows electric field distribution along the channel. A graph 204 shows entropy (S) of DNA along the channel. A graph 206 shows electrostatic energy (U) and the Gibbs free energy (G=U−T*S) of DNA, where T represents the thermodynamic temperature in an absolute scale, e.g., Kelvin. In the graph 206, qV is indicated where q is charge and V is voltage.

The spherical cap has a gradually changed height and thus yields a gradually changing channel depth, with the smallest depth at a zenith of the spherical cap. The electrical field reaches a peak value at the shallowest channel depth region (graph 202). As a biopolymer enters from a deep channel region and moves into a shallowest region of the channel (at the zenith), it stretches as the channel depth reduces with its entropy value (S) gradually decreasing (graph 204). This yields a smooth changing Gibbs free energy (G=U−TS) slope (graph 206), where U is the electrostatic energy of the charged biopolymer and T is the temperature. Therefore, the smoothly transitioned channel depth leads to a minimized entropic energy barrier for the biopolymers to transport through the channel, which is important for the translocation and stretching of biopolymers.

Figure 3:
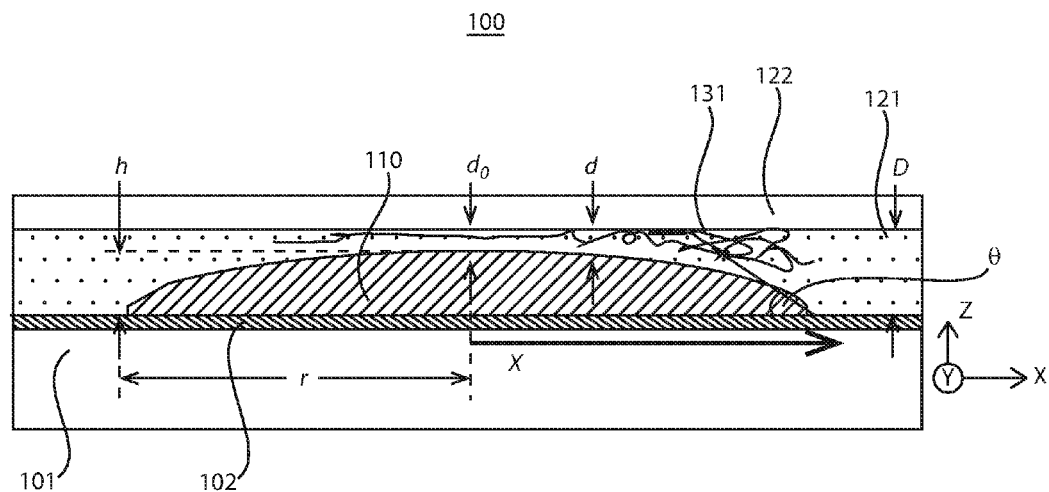
FIG. 3 is a cross-sectional view of a fluidic channel device with gradually changing depth showing controlling of the nano-fluidic channel depth by tuning parameters such as a contact angle of a surface relief on the substrate, radius of the curvature of the reflowed surface relief material, a size of the reflowed material cap, and a height of the reflowed material cap in accordance with the present principles.

Referring to FIG. 3, in one embodiment, the surface relief material 110 is completely melted to an ideal spherical cap. Nano-fluidic channel depth is controlled by tuning the contact angle of a surface relief on the substrate. R is the radius of the curvature of the reflowed surface relief material, θ is the contact angle, r is the size of the reflowed material cap, h is the height of the reflowed material cap, $d_0$ is the minimal channel depth, d is the variable channel depth along the x direction, D is the maximum channel depth. In this case, the relationships between the radius of curvature R, the cap height h, the cap size r and the contact angle θ may include the following: $(R-h)^2+r^2=R^2$, $r=R*\sin(\theta)$; $h_0=R-R*\cos(\theta)$.

Assuming the volume of the surface relief material V is conserved, the volume of the spherical cap V can be written as:

$$V=\pi/6*h*(3r^2+h^2)=\pi/3*h^2*(3R-h)=\pi/3*R^3*(2-3*\cos(\theta)+\cos(\theta)^3)=V_0$$

From above, it is clear R can be derived from the initial volume $V_0$ with the contact angle θ given. Then, h and r can be calculated from R and θ. Assuming the nanochannel is sealed with a flat film (122 in FIG. 1A), the smallest depth is $d_0$, and the channel depth d or d(x) along the x direction can be calculated as $d(x)=d_0+(R-\sqrt{R^2-x^2})$. This geometry is illustrative as other geometries are also contemplated and with the scope of the present principles.

Figure 4:
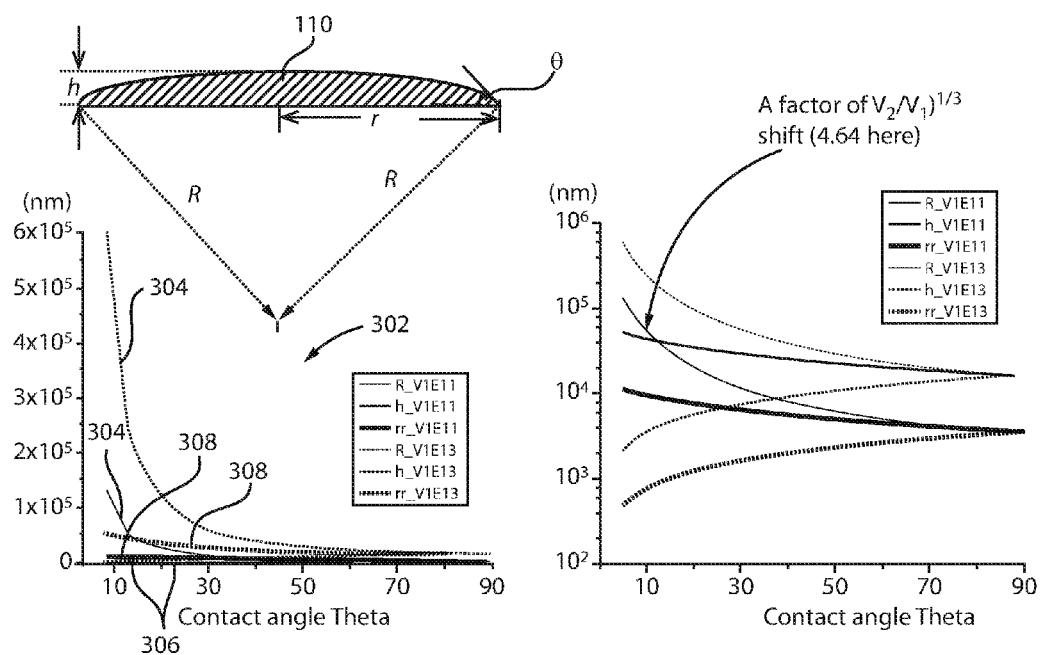
FIG. 4 shows linear plots and log plots of radius of the curvature R, height h, and a size of the reflowed material cap r as a function of contact angle with given volumes in accordance with the present principles.

Referring to FIG. 4, where the surface relief material 110 is completely melted to an ideal spherical cap, the parameters R, r, and h are all calculated at different contact angles. Two samples of initial volumes for the surface relief material 110 were used, $V_1=10^2$ μm$^3$ (e.g., 1*10*10 μm$^3$ or $10^{11}$ nm$^3$) and $V_2=10^4$ μm$^3$ (e.g., 1*100*100 μm$^3$ or $10^{13}$ nm$^3$). In fact, the 100 times difference in volume causes a 4.64 (=$(V_2/V_1)^{1/3}$) times difference in the two sets of curves of R, r, and h.

Examples for determining geometrical parameters R, h, and r by volume and contact angle include a first graph 302, which is a linear plot showing R 304, h 306, and r 308 as a function of contact angle (θ) with given volumes ($V_1=1\times10^{11}$, solid lines, and $V_2=1\times10^{13}$ nm$^3$, dashed lines), and a second graph 310, which plots of R 312, h 314, and r 316 as a function of contact angle (θ) with given volumes ($V_1=1\times10^{11}$, solid lines, and $V_2=1\times10^{13}$ nm$^3$, dashed lines). r is related to channel depth.

Figure 5:
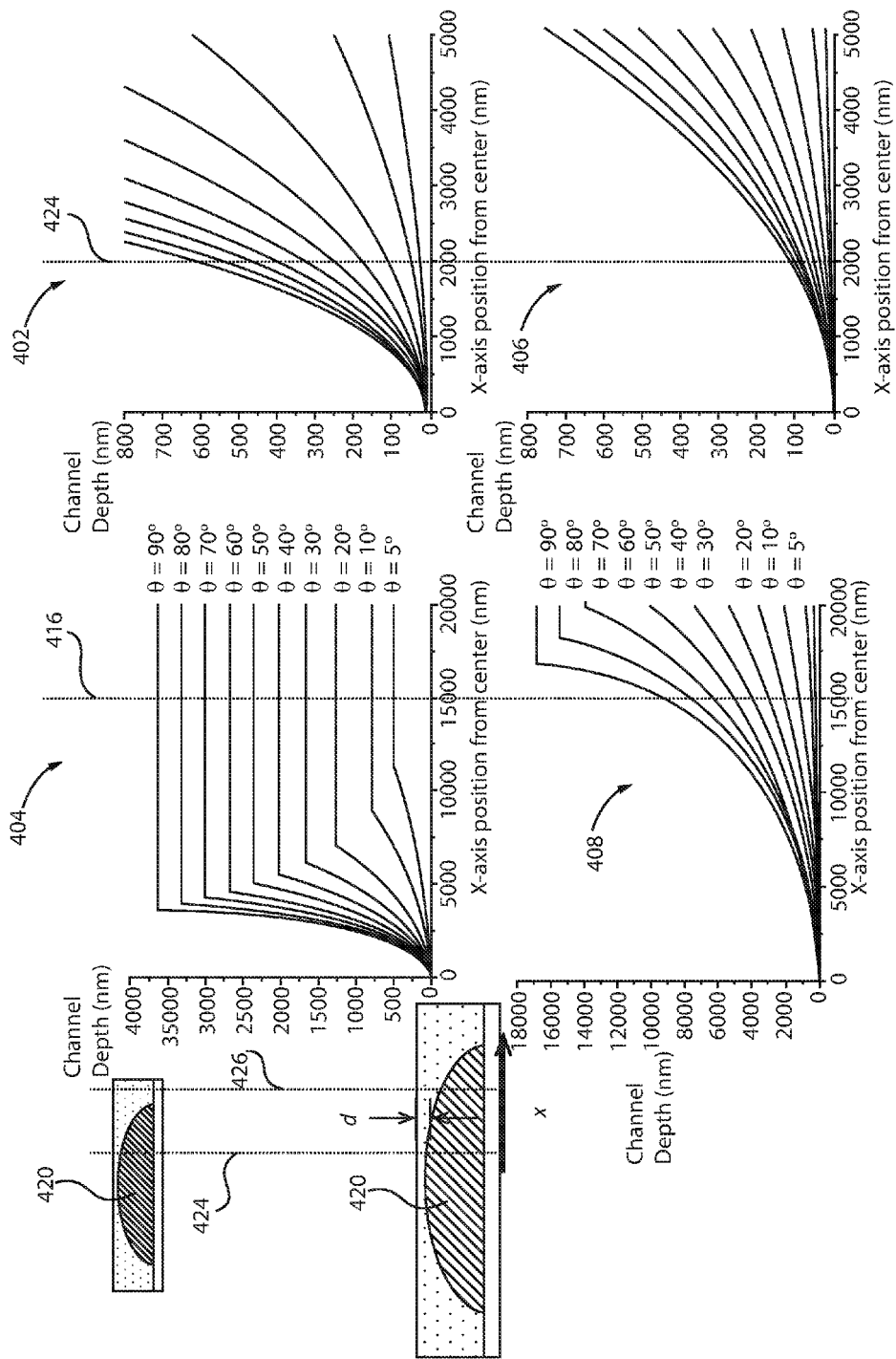
FIG. 5 shows graphs of channel depth versus x position for controlling nanochannel depths by volume and contact angle (5-90°) for volumes $V_1$ and $V_2$, and contact angles along the x-axis from 0 to 20 μm; and along the x-axis from 0 to 5 μm in accordance with the present principles.

Referring to FIG. 5, examples for controlling nanochannel depths by volume and contact angle are illustratively shown. A graph 402 shows channel depths with different contact angles (5-90°) for a cap 420 (surface relief material 110) with a volume $V_1=1\times10^{11}$ nm$^3$ along the x-axis from 0 to 20 μm (indicated by line 424) from a center position of the cap 420. A graph 404 shows channel depths with different contact angles) (5-90°) for the cap 420 with a volume $V_1=1\times10^{11}$ nm$^3$ along x-axis from 0 to 5 μm (indicated by line 426). A graph 406 shows channel depths with different contact angles) (5-90°) for a cap 422 with a volume $V_2=1\times10^{13}$ nm$^3$ along the x-axis from 0 to 20 μm (indicated by line 424) from a center position of the cap 422. A graph 408 shows channel depths with different contact angles (5-90°) for the cap 422 with a volume $V_2=1\times10^{13}$ nm$^3$ along x-axis from 0 to 5 μm (indicated by line 426).

A nanochannel depth (d) can be determined assuming two volumes of the surface relief material (110) for caps 420 and 422 as $10^{11}$ nm$^3$ (graphs 402, 404) and $10^{13}$ nm$^3$ (graphs 406, 408). The channel depth d increases very smoothly with a small contact angle θ, but increases quite dramatically for large contact angles. An initial volume of the surface relief material (110) for caps 420, 422 also has an impact on the nanochannel depth slope. At a large distance away from the cap center where x=0, for example x=15 μm, the channel depth is larger for a larger cap. This is because the depth is fixed as the maximum channel depth D=h+$d_0$ for a small cap, and the channel depth increases as a function of x because of a greater r and h for a larger cap. At a small distance away from the cap center where x=0, for example x=2 µm, the channel depth is larger for a small cap. This is because the cap height changes more abruptly over a same distance x.

This shows that the cap geometry and the channel depth can flexibly be designed by tuning the contact angle and the surface relief material (110). In practical embodiments, the channel depth may need to change from <5 nm to 100-500 nm over a distance of 1-100 µm. The contact angle and the volume of the surface relief material can be determined according to the corresponding h and r dimensions.

Referring to FIGS. 6A-6H, a fabrication scheme is illustratively shown to achieve such a channel-on-cap configuration for a nanodevice 100. An example of fabricating nanochannels on a reflowed surface relief material includes depositing a surface layer to control contact angle, patterning surface relief materials and annealing to reflow surface relief materials. A thin dielectric coating is deposited and a thick insulating dielectric material is formed on top. A chemical mechanical planarization (CMP) and reactive ion etch (RIE) are employed to reduce the thickness of insulating channel dielectric layer. Nano-fluidic channels are patterned, and sealed. Each of FIGS. 6A-6H include a cross-section view (CS), a top view (TV), and a set of axes X, Y and Z for each view.

Figure 6A:
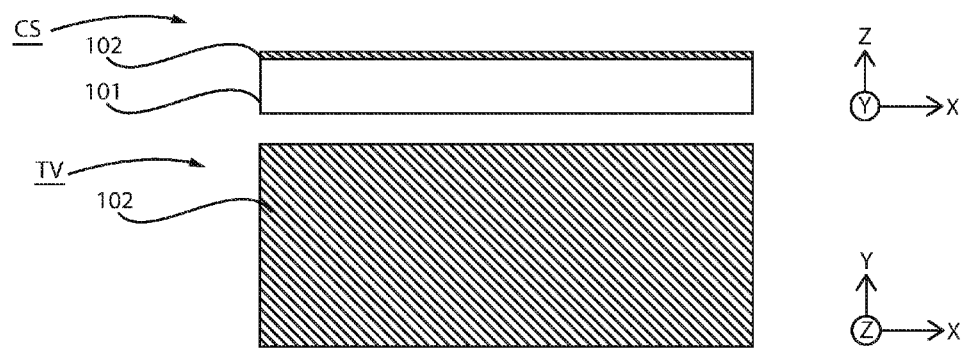
FIG. 6A is a cross-sectional view and a top view of a substrate having a dielectric or surface layer formed thereon to control contact angle in accordance with the present principles.

Referring to FIG. 6A, a dielectric layer 102 is deposited on top of a substrate material 101. The dielectric layer 102 is employed as an insulating coating of a nanochannel bottom surface, and is also employed as a layer to flexibly tune the contact angle of surface relief material. The dielectric layer 102 can be either organic or inorganic, it can be realized by physical deposition, chemical deposition, chemical assembly, etc., and the material of dielectric layer 102 may include, e.g., $SiO_2$, $Al_2O_3$, $Si_3N_4$, organic monolayer, etc. The material of substrate 101 can be any material, either organic or inorganic, and it can be, e.g., Si, $SiO_2$, $Si_3N_4$, metal, plastic, etc. The dielectric layer (surface layer) 102 controls the surface tension, which in turn determines the contact angle and the shape of reflowed materials.

Figure 6B:
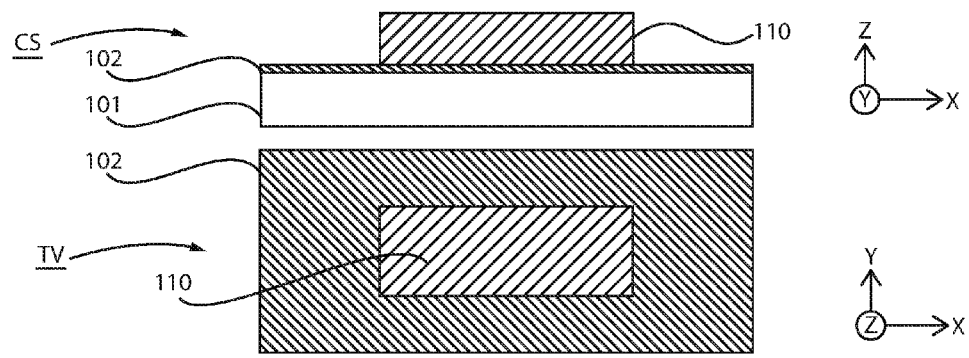
FIG. 6B is a cross-sectional view and a top view of the device of FIG. 6A showing surface relief materials patterned on the surface layer or substrate in accordance with the present principles.

Referring to FIG. 6B, a surface relief material 110 is patterned by a combination of micro-nano fabrication techniques, which may include lithography, deposition, etching, etc. An initial volume of the surface relief material 110 is determined in this process. The shape of the surface relief material 110 does not have to be square or rectangular.

Figure 6C:
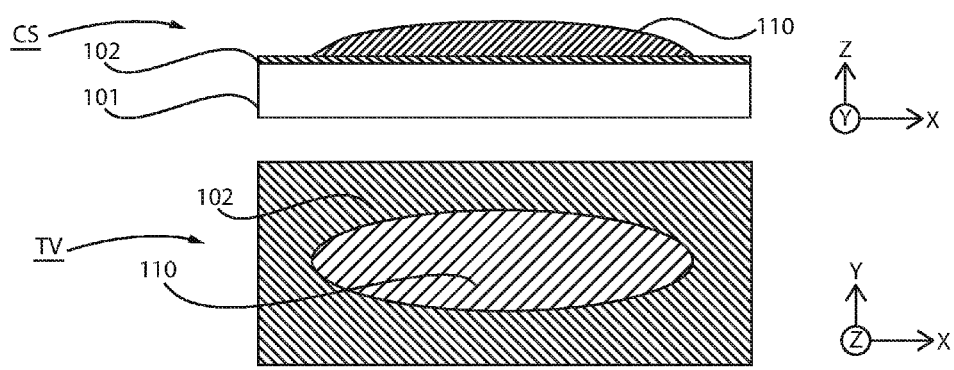
FIG. 6C is a cross-sectional view and a top view of the device of FIG. 6B showing an anneal to reflow surface relief materials in accordance with the present principles.

Referring to FIG. 6C, an annealing process is performed to fully or partially melt the surface relief material 110 to form a cap. The annealing method can be light illumination (e.g., ultraviolet (UV), excimer, visible, infrared (IR), etc.), heat, etc. Preferably, the heating temperature exceeds the melting or glass-transition temperature of the material to fully reflow the material, which makes the material round, preferably in three dimensions. The temperature could also be slightly lower than the melting or glass-transition temperature to only soften the surface relief material. The surface relief material does not have to be round. A localized heat is also possible to partially melt the surface relief pattern. In an alternate embodiment, the surface relief material 110 is formed separately and adhered to the dielectric layer 102.

Figure 6D:
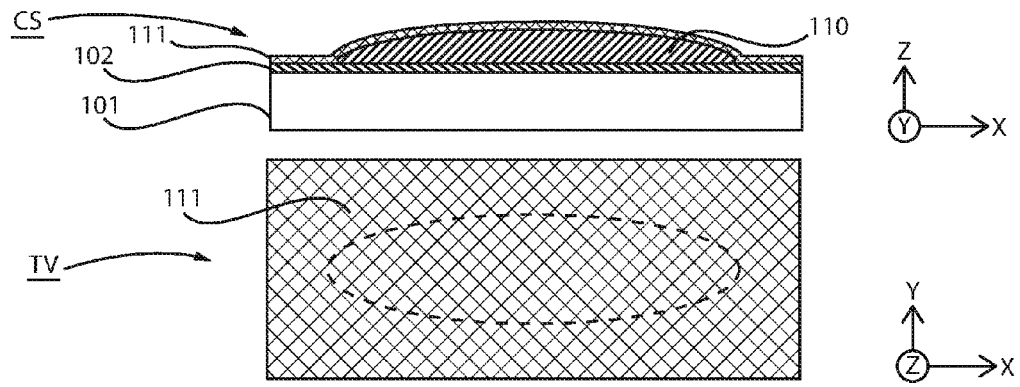
FIG. 6D is a cross-sectional view and a top view of the device of FIG. 6C showing a deposition of a thin dielectric coating in accordance with the present principles.

Referring to FIG. 6D, the annealed surface relief cap (110) is optionally coated with another dielectric layer 111. The coating or dielectric layer material may include, e.g., $Al_2O_3$, $SiO_2$, etc. The deposition can be by atomic layer deposition (ALD), plasma enhanced chemical vapor deposition (PECVD), low pressure CVD (LPCVD), evaporation, etc. The coating material or dielectric layer 111 can be used to harden the underlying surface-relief cap (110), protect the cap (110) from etching that follows, and act as an etch-stop layer to control channel depth.

Figure 6E:
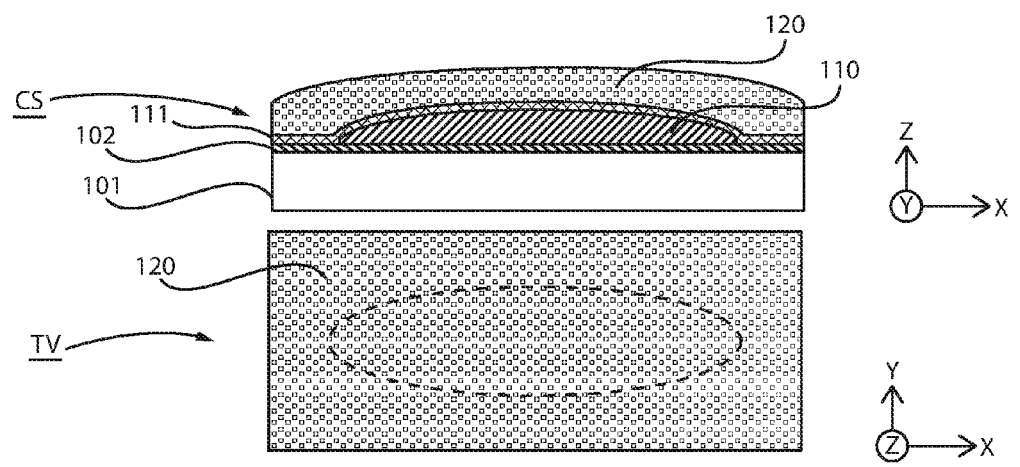
FIG. 6E is a cross-sectional view and a top view of the device of FIG. 6D showing a deposition of a thick insulating dielectric material in accordance with the present principles.

Referring to FIG. 6E, an insulating dielectric layer 120 is coated on top of the spherical cap 110 or dielectric layer 111, if employed. Layer 120 is to be used to form a fluidic channel. The insulating dielectric layer 120 (channel material) may include, e.g., $SiO_2$, $Si_3N_4$, etc.

Figure 6F:
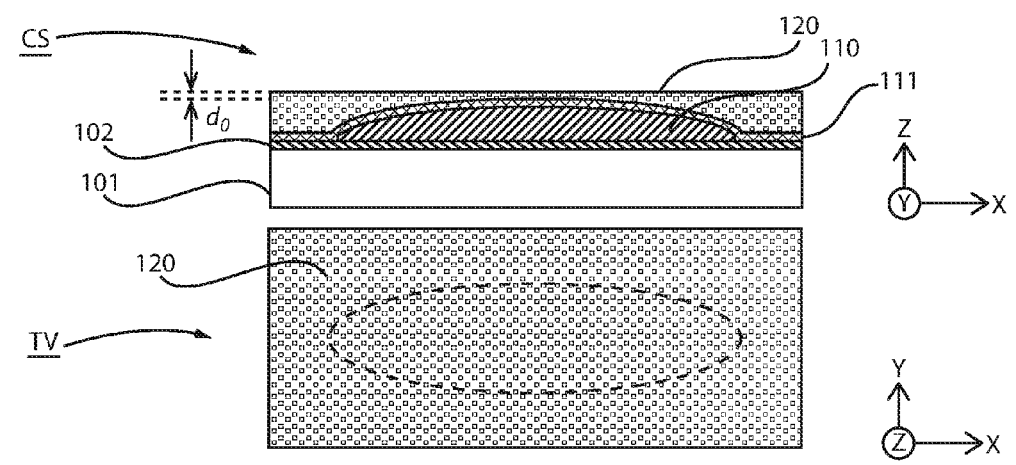
FIG. 6F is a cross-sectional view and a top view of the device of FIG. 6E showing a chemical mechanical polish (CMP) planarization and reactive ion etch (RIE) to reduce a thickness of insulating channel dielectric layer in accordance with the present principles.

Referring to FIG. 6F, the insulating dielectric layer 120 is planarized by polishing (e.g., CMP) and optionally thinned by etching, e.g., reactive ion etching or wet chemical etching. The minimum dielectric layer height is set to do, which may be, e.g., less than 100 nm and preferably less than 20 nm.

Figure 6G:
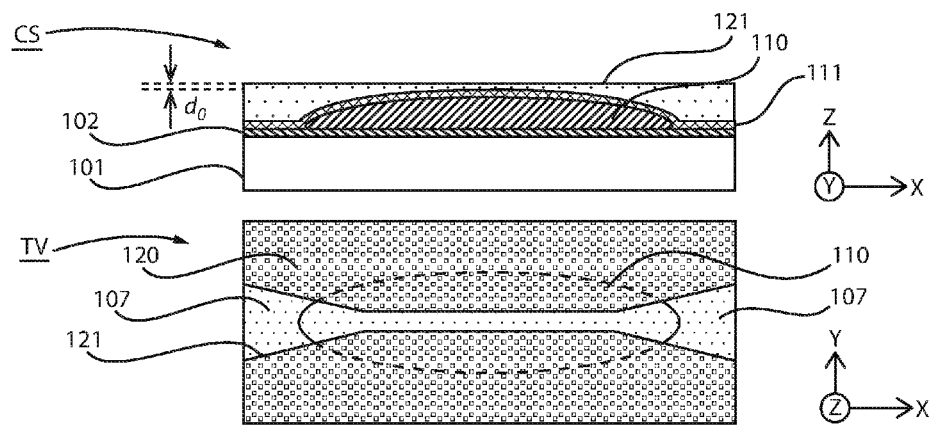
FIG. 6G is a cross-sectional view and a top view of the device of FIG. 6F showing patterning of a nano-fluidic channel in accordance with the present principles.

Referring to FIG. 6G, a nano-channel 121 is patterned and aligned on top of the spherical cap (110) region by a series of micro-nano fabrication techniques, which may include lithography, deposition, etching, etc. The nanochannels 121 may have different widths at different regions, e.g., with the smallest dimensions on top of the center of the spherical cap 110. The nano-channel 121 may be configured with tapers 107 or other features to assist in loading and translocating biopolymers.

Figure 6H:
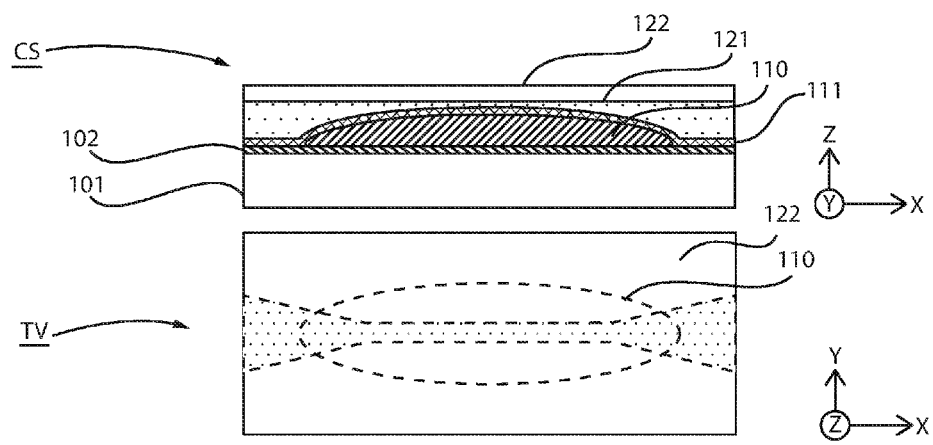
FIG. 6H is a cross-sectional view and a top view of the device of FIG. 6G showing sealing of nano-fluidic channels in accordance with the present principles.

Referring to FIG. 6H, the channels 121 are sealed with a dielectric material 122. The sealing method may include wafer bonding and/or pitching off small venting holes using a sacrificial channel material.

Figure 7:
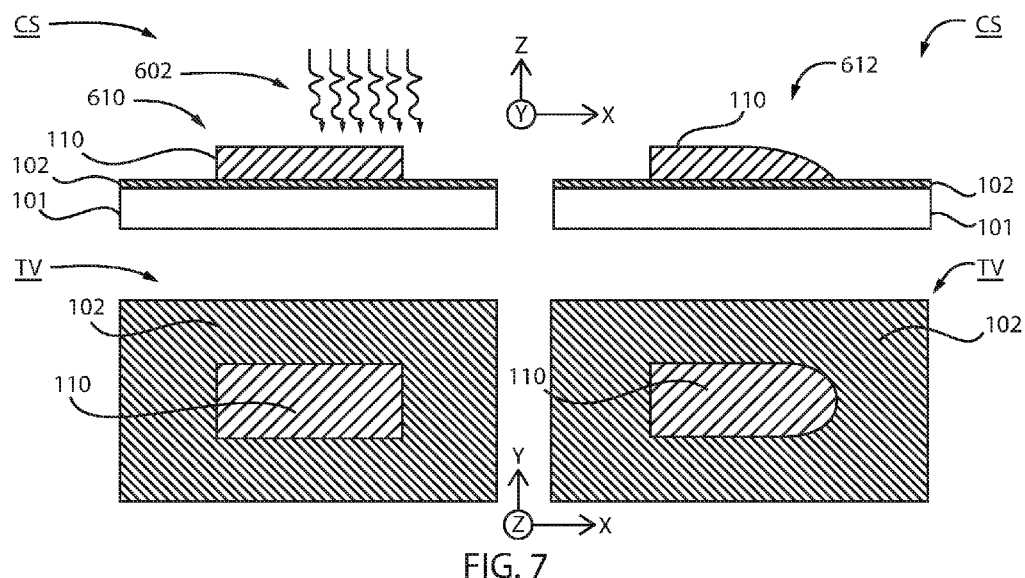
FIG. 7 is a cross-sectional view and a top view of devices showing local heating of surface relief materials before and after heating in accordance with the present principles.

Referring to FIG. 7, in another embodiment, the cap may be formed using different heating techniques to result in different shapes. Local heating of surface relief materials is shown during heating (610) and after heating (612). A localized heat source 602, e.g., a laser or focused light, can be employed to locally modify a shape of surface relief materials 110. This can result in arbitrary and asymmetric channel depth profiles.

Figure 8A:
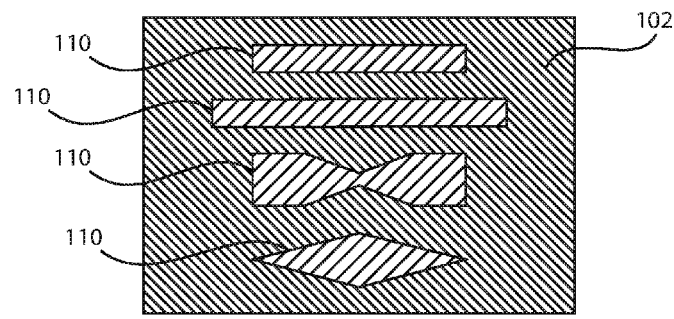
FIG. 8A is a top view showing different shapes, surface densities and locations of surface relief material structures in accordance with the present principles.

Referring to FIG. 8A, in other embodiments, structure geometry, dimension, and patterning density of the surface relief patterns (110) can be flexibly changed, according to the need for different dimensions and densities for different channel applications. Tuning shapes, surface density, and locations of surface relief material structures may include complex compound surfaces and shapes. Structures other than those depicted in FIG. 8A are also contemplated.

Figure 8B:
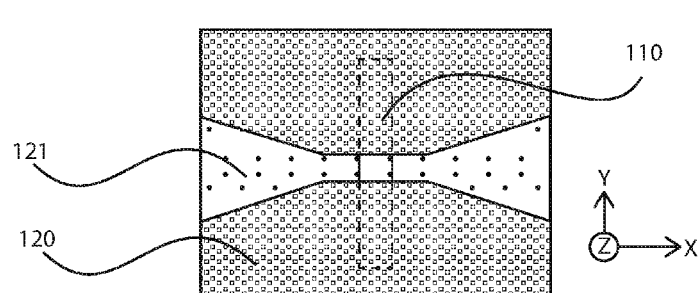
FIG. 8B is a top view showing a transverse bar shape rounded in accordance with the present principles.

Referring to FIG. 8B, in one practical embodiment, surface relief material 110 can be patterned as a very long (e.g., 1-10 µm length) bar along the Y direction (shown under the insulating dielectric layer 120). In this way, the melted surface relief material is less spherical but rather cylindrical with a uniform round cap along the Y direction. The nano-channel 121 can be very easily aligned to the surface relief materials 110 (if the top cap is very spherical then the lateral lithography alignment to pattern the nanochannels on top of the cap would be very stringent).

Figure 9A:
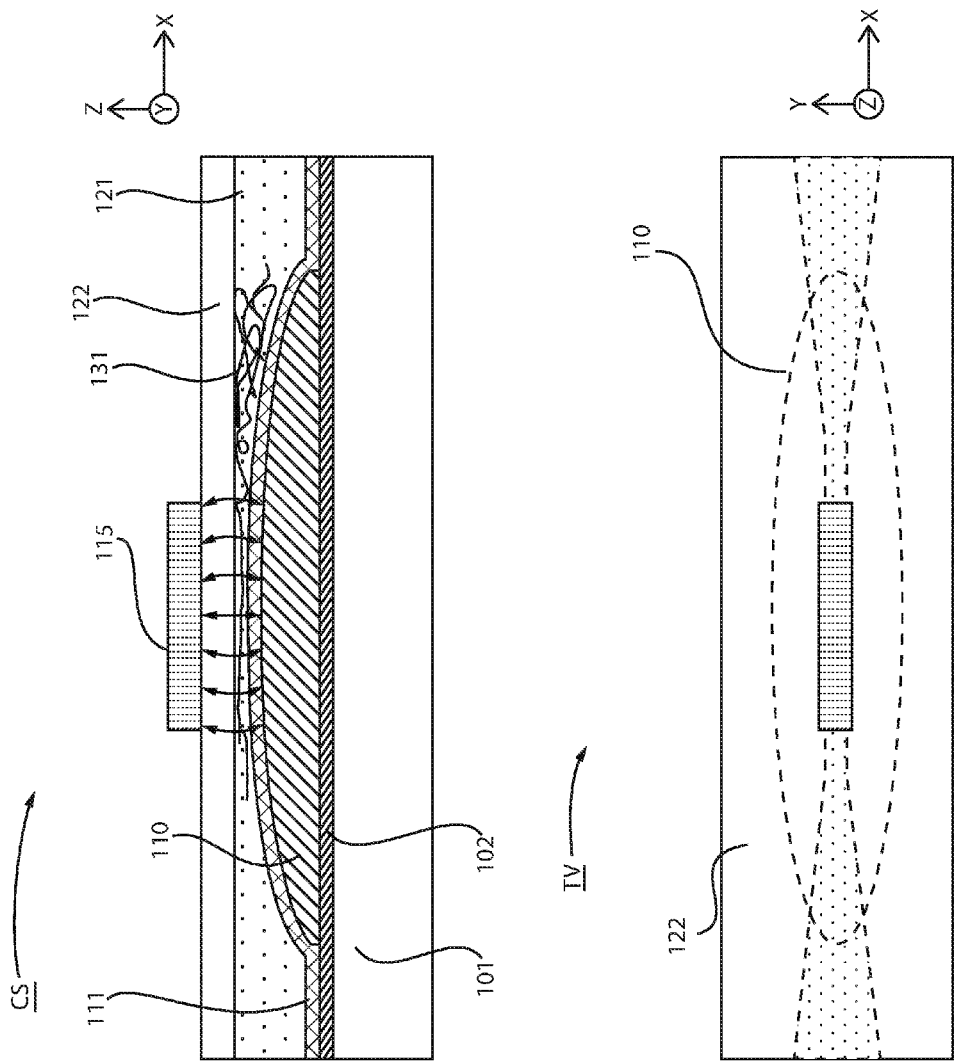
FIG. 9A is a cross-sectional view showing integration of electrodes on nanochannels of surface relief materials including single top-bottom electrodes, where the bottom electrode can be the surface relief material in accordance with the present principles.
Figure 9B:
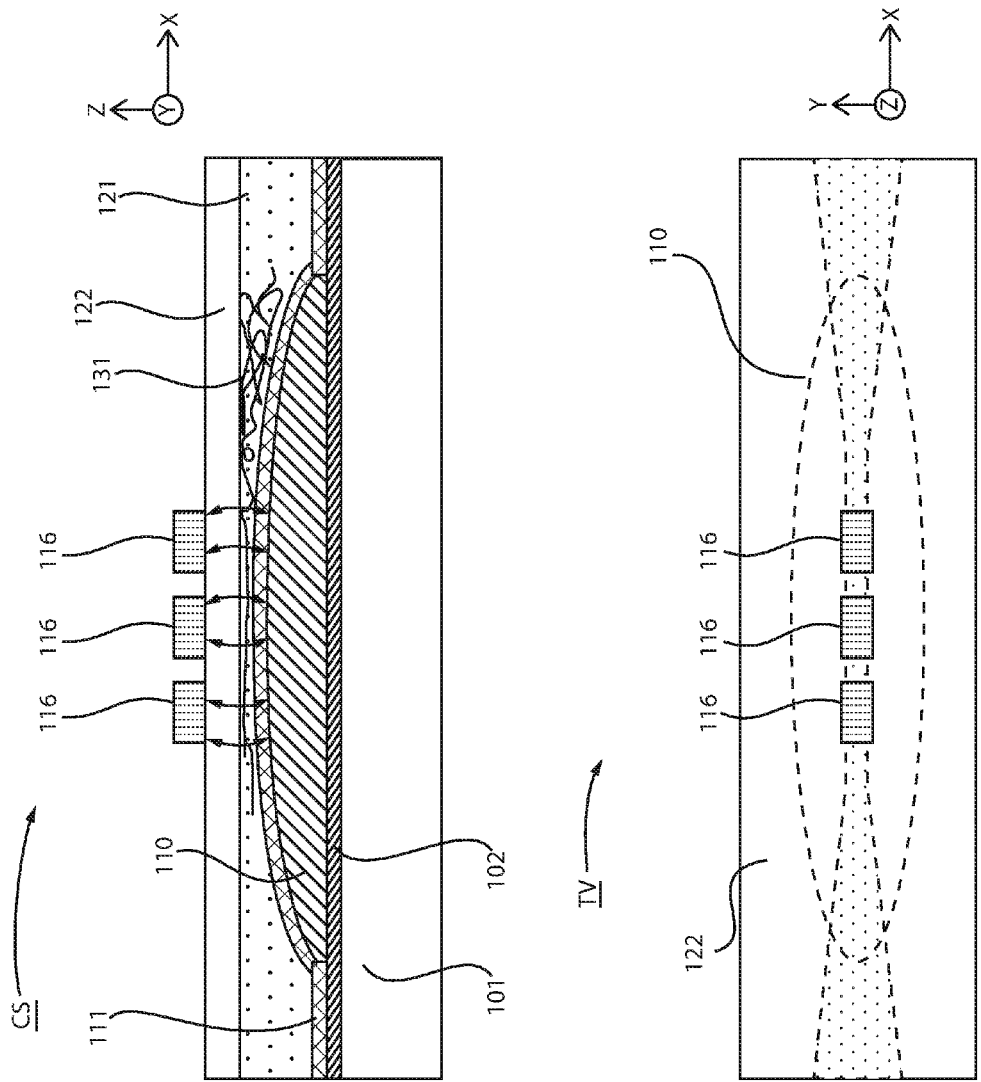
FIG. 9B is a cross-sectional view showing integration of electrodes on nanochannels of surface relief materials including multiple top-bottom electrodes, where the bottom electrode can be the surface relief material in accordance with the present principles.
Figure 9C:
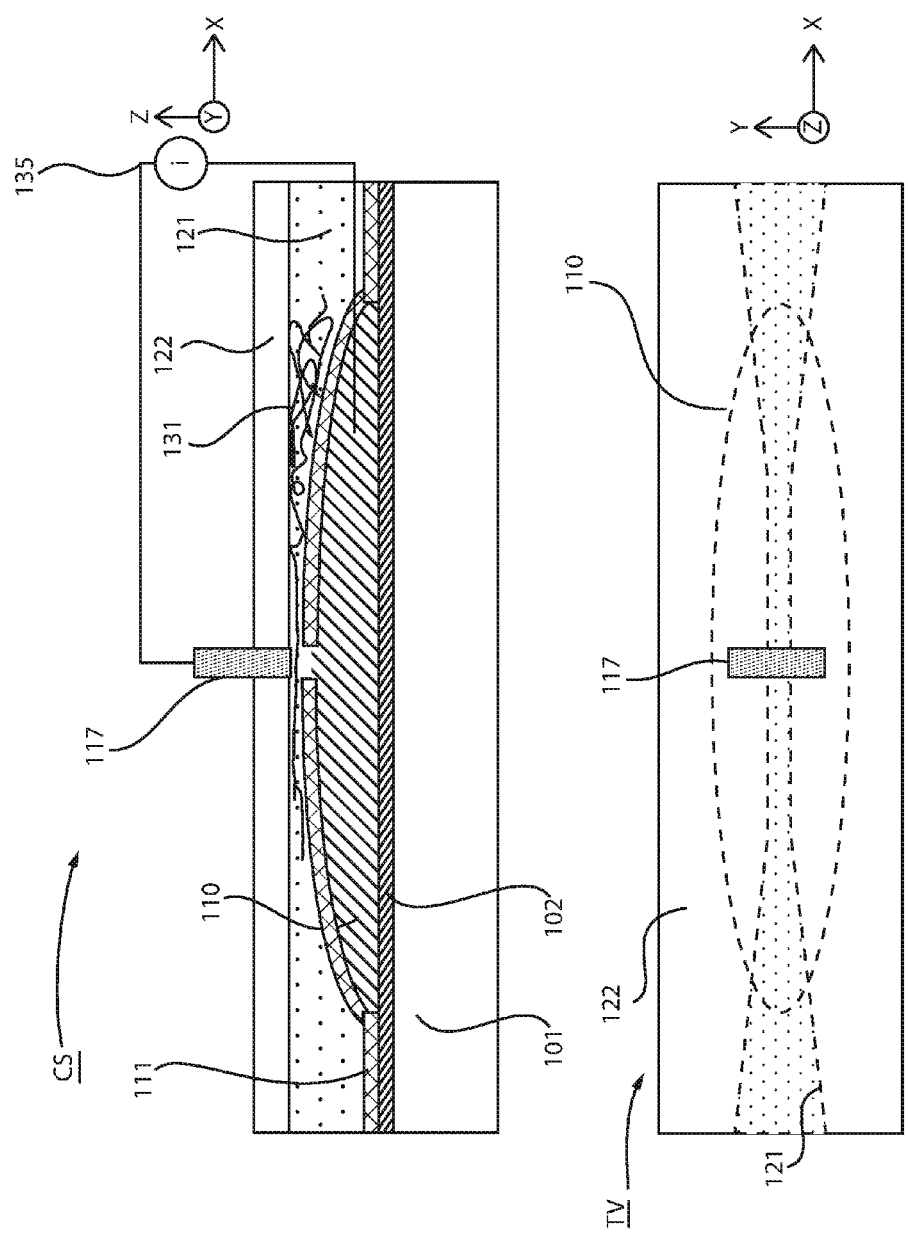
FIG. 9C is a cross-sectional view showing integration of electrodes on nanochannels of surface relief materials including molecular sensing electrodes, where the bottom electrode can be the surface relief material in accordance with the present principles.

Referring to FIGS. 9A-9C, the nanodevices in accordance with the present principles may be configured in a plurality of ways, e.g., by including electrodes or other structures for driving or controlling biopolymers or other molecules. Integrating electrodes with nanochannels on surface relief materials may include single top-bottom electrodes, where the bottom electrodes can be the surface relief material itself, may be embedded in or on the surface relief material, may include multiple top and bottom electrodes, may include molecular sensing electrodes, etc.

Referring to FIGS. 9A and 9B, the surface relief structures 110 can be integrated with electrodes for better control of biopolymers and/or sensing the biopolymers. The surface relief material itself can be employed as an electrode. This may include coating the surface relief material 110 with a conductive material, placing a conductor in the surface relief material 110, making the surface relief material 110 from a conductive material, or provide electrical conductors coated with a layer of linker molecules.

A top electrode 115 and/or 116 may be deposited and patterned or otherwise adhered to the dielectric layer 122. A method for controlling a biopolymer 131 passing between the electrode 115 and the surface relief material 110 can be based on electrostatic interaction of the charged biopolymer with applied electrical potential. There can be multiple electrodes 116 (FIG. 9B) or a single (FIG. 9A) top electrode. In one embodiment, the surfaces of electrodes 115 and 116 can be functioned (lined or coated) with organic molecules or linker molecules which can interact with the biopolymer, for example, to hold the biopolymer, sense the biopolymer or otherwise interact with the biopolymer being stretched or sensed. The linker molecules may include with self-assembled molecules with a functional head-group, such as, e.g., benzamide and/or imidazole. Other linker molecules may be employed as well.

Referring to FIG. 9C, in another embodiment, a sensing circuit 135 may be connected between an electrode 117 and the surface relief material 110 to form an ohmic contact using fluid in the channel 121. Electrical current signals can be used to detect and even sequence the biopolymer 131 as it moves through the channel 121. Other configurations are also contemplated.

It should be understood that the biopolymers may employ electrophoresis to drive or translocate biopolymers 131. The motion of dispersed particles, under the influence of a spatially uniform electric field, is employed to move, relative to a fluid disposed in the channel 121, the biopolymer through the nanochannel 121.

It should also be noted that, in some alternative implementations, the functions noted in the figures may occur out of the order noted in the figures. For example, two steps shown in succession may, in fact, be executed substantially concurrently, or the steps may sometimes be executed in the reverse order, depending upon the functionality involved.

Having described preferred embodiments for nanofluidic channels with gradual depth change for reducing entropic barrier of biopolymers (which are intended to be illustrative and not limiting), it is noted that modifications and variations can be made by persons skilled in the art in light of the above teachings. It is therefore to be understood that changes may be made in the particular embodiments disclosed which are within the scope of the invention as outlined by the appended claims. Having thus described aspects of the invention, with the details and particularity required by the patent laws, what is claimed and desired protected by Letters Patent is set forth in the appended claims.

What is claimed is:

1. A microfluidic channel, comprising:
    a cap having a rounded surface on a substrate;
    an insulating dielectric layer formed over the cap having a gradually changing thickness between the rounded surface and a top surface of the insulating dielectric layer; and
    a nanochannel formed in the insulating dielectric layer, wherein the nanochannel is aligned with the rounded surface of the cap.

2. The microfluidic channel of claim 1, further comprising a top dielectric layer over the channel dielectric layer to seal the nanochannel.

3. The microfluidic channel of claim 1, further comprising a surface coating layer on the substrate that controls the surface tension of the surface between the substrate and the cap.

4. The microfluidic channel of claim 1, wherein the cap has a long axis and a short axis, and the nanochannel is aligned parallel with the long axis of the cap.

5. The microfluidic channel of claim 1, wherein the cap has a long axis and a short axis, and the nanochannel is aligned perpendicular with the long axis of the cap.

6. The microfluidic channel of claim 1, wherein the nanochannel in the insulating dielectric layer has at least one end tapered to assist in loading a biopolymer into the nanochannel.

7. The microfluidic channel of claim 1, further comprising electrodes adjacent to the nanochannel for controlling and/or sensing a biopolymer.

8. The microfluidic channel of claim 1, further comprising a dielectric coating on the cap between the top surface of the cap and the insulating dielectric layer, wherein the dielectric coating is a different material than the insulating dielectric layer.

9. A microfluidic channel, comprising: a cap having a rounded surface on a substrate;
    a dielectric layer disposed between the substrate and the cap having the rounded surface;
    an insulating dielectric layer over the cap;
    a nanochannel in the insulating dielectric layer, wherein the nanochannel is aligned with the rounded surface of the cap, and has at least one end tapered to assist in loading a biopolymer into the nanochannel; and
    a top dielectric layer over the channel dielectric layer to seal the nanochannel.

10. The microfluidic channel of claim 9, wherein a radius of curvature of the rounded surface of the cap is determined by a contact angle with the dielectric layer disposed between the substrate and the cap having the rounded surface.

* * * * *